(12) United States Patent
Wang et al.

(10) Patent No.: US 8,439,909 B2
(45) Date of Patent: May 14, 2013

(54) COOLED ABLATION CATHETER WITH RECIPROCATING FLOW

(75) Inventors: Huisun Wang, Maple Grove, MN (US); Jeremy D. Dando, Plymouth, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 0 days.

(21) Appl. No.: 13/093,508

(22) Filed: Apr. 25, 2011

(65) Prior Publication Data

US 2011/0202054 A1    Aug. 18, 2011

Related U.S. Application Data

(62) Division of application No. 11/646,255, filed on Dec. 28, 2006, now Pat. No. 7,951,143.

(51) Int. Cl.
*A61B 18/14* (2006.01)
(52) U.S. Cl.
USPC .............................................. 606/41; 606/45
(58) Field of Classification Search .............. 606/41; 604/99.04, 245, 249, 269
See application file for complete search history.

(56) References Cited

U.S. PATENT DOCUMENTS

| | | |
|---|---|---|
| 3,331,371 A | 7/1967 | Rocchi et al. |
| 3,671,979 A | 6/1972 | Moulopoulos |
| 4,084,606 A | 4/1978 | Mittleman |
| 4,841,984 A | 6/1989 | Armeniades et al. |
| 4,857,054 A | 8/1989 | Helfer |
| 5,056,517 A | 10/1991 | Fenici |
| 5,112,301 A * | 5/1992 | Fenton et al. ............... 604/30 |
| 5,230,349 A | 7/1993 | Langberg |
| 5,290,263 A | 3/1994 | Wigness et al. |
| 5,348,554 A | 9/1994 | Imran et al. |
| 5,403,276 A | 4/1995 | Schechter et al. |
| 5,423,811 A | 6/1995 | Imran et al. |
| 5,427,114 A | 6/1995 | Colliver et al. |
| 5,462,521 A | 10/1995 | Brucker et al. |
| 5,545,161 A | 8/1996 | Imran |
| 5,643,197 A | 7/1997 | Brucker et al. |
| 5,660,205 A | 8/1997 | Epstein |
| 5,697,927 A | 12/1997 | Imran et al. |
| 5,792,140 A | 8/1998 | Tu et al. |
| 5,843,152 A | 12/1998 | Tu et al. |
| 5,913,856 A | 6/1999 | Chia et al. |
| 5,971,968 A | 10/1999 | Tu et al. |
| 6,017,338 A | 1/2000 | Brucker et al. |
| 6,044,845 A | 4/2000 | Lewis |
| 6,602,242 B1 | 8/2003 | Fung et al. |

(Continued)

FOREIGN PATENT DOCUMENTS
WO    WO-2005/048858    6/2005

*Primary Examiner* — Linda Dvorak
*Assistant Examiner* — Jaymi Della
(74) *Attorney, Agent, or Firm* — Dykema Gossett PLLC (57) ABSTRACT

The invention relates to an ablation catheter which controls the temperature and reduces the coagulation of biological fluids on an electrode of a catheter, prevents the impedance rise of tissue in contact with the electrode, and maximizes the potential energy transfer to the tissue, thereby allowing an increase in the lesion size produced by the ablation. The electrode includes passages positioned to allow blood and other biological fluids to flow into and out of an inner cavity of the electrode. This fluid flow produced the desired cooling effect and is accomplished, for example, by a reciprocating plunger or piston, or by a balloon that is alternately inflated and deflated.

17 Claims, 4 Drawing Sheets

U.S. PATENT DOCUMENTS

| | | |
|---|---|---|
| 6,611,699 B2 | 8/2003 | Messing |
| 6,659,959 B2 | 12/2003 | Brockway et al. |
| 6,955,675 B2 | 10/2005 | Jain |
| 7,025,742 B2 | 4/2006 | Rubenstein et al. |
| 7,166,105 B2 | 1/2007 | Mulier et al. |
| 2002/0026188 A1* | 2/2002 | Balbierz et al. ............ 606/41 |
| 2002/0058933 A1* | 5/2002 | Christopherson et al. ...... 606/34 |
| 2002/0120261 A1* | 8/2002 | Morris et al. .................. 606/41 |
| 2002/0177846 A1 | 11/2002 | Mulier et al. |
| 2003/0014035 A1 | 1/2003 | Trombley et al. |
| 2003/0225364 A1 | 12/2003 | Kraft et al. |
| 2004/0030279 A1 | 2/2004 | Rubenstein et al. |
| 2004/0098022 A1 | 5/2004 | Barone |
| 2004/0102825 A1 | 5/2004 | Daoud |
| 2004/0176801 A1 | 9/2004 | Edwards et al. |
| 2005/0049453 A1 | 3/2005 | Faulkner |
| 2005/0085769 A1 | 4/2005 | MacMahon et al. |
| 2005/0137659 A1* | 6/2005 | Garabedian et al. ............ 607/96 |
| 2005/0143798 A1 | 6/2005 | Bleam et al. |
| 2005/0149116 A1 | 7/2005 | Edwards et al. |
| 2005/0209580 A1 | 9/2005 | Freyman |
| 2005/0256521 A1 | 11/2005 | Kozel |
| 2006/0036303 A1 | 2/2006 | Schwartz |
| 2006/0058775 A1 | 3/2006 | Stevens et al. |
| 2006/0058854 A1 | 3/2006 | Abrams et al. |
| 2006/0229599 A1 | 10/2006 | Rashidi |
| 2006/0278248 A1 | 12/2006 | Viswanathan |
| 2007/0270791 A1 | 11/2007 | Wang et al. |

* cited by examiner

COOLED ABLATION CATHETER WITH RECIPROCATING FLOW

CROSS-REFERENCE TO RELATED APPLICATIONS

This application is a divisional application of U.S. application Ser. No. 11/646,255, filed 28 Dec. 2006, (the '255 application), now pending. This application is also related to U.S. application Ser. No. 11/646,275, filed 28 Dec. 2006, (the '275 application), now U.S. Pat. No. 7,951,143, U.S. application Ser. No. 11/646,237, filed 28 Dec. 2006 (the '237 application), now U.S. Pat. No. 7,824,406, and U.S. application Ser. No. 11/646,270, filed 28 Dec. 2006 (the '270 application), now U.S. Pat. No. 7,591,816. The '255 application, '275 application, '237 application, and '270 application are each hereby incorporated by reference as though fully set forth herein.

BACKGROUND OF THE INVENTION a. Field of the Invention

The instant invention relates to catheters. In particular, the instant invention relates to an irrigated ablative catheter tip with reciprocating flow.

b. Background Art

Electrical stimulation of myocardial tissue controls the pumping action of the heart. Stimulation of this tissue in various regions of the heart is controlled by a series of conduction pathways contained within the myocardial tissue. In a healthy heart, contraction and relaxation of the heart muscle (myocardium) occur in an organized fashion as electrochemical signals pass sequentially through the myocardium from the sinoatrial (SA) node, which consists of a bundle of unique cells disposed in the wall of the right atrium, to the atrioventricular (AV) node, and then into the left and right ventricles via a route that includes the His-Purkinje system. The AV node is located near the ostium of the coronary sinus in the interatrial septum in the right atrium. Each cell membrane of the SA node has a characteristic tendency of a gradual leak of sodium ions over time leading to a periodic break down of the cell membrane periodically, thus allowing an inflow of sodium ions, and thereby causing the SA node cells to depolarize. The SA node cells are in communication with the surrounding atrial muscle cells such that the depolarization of the SA node cells causes the adjacent atrial muscle cells to also depolarize. This depolarization results in atrial systole, during which the atria contract to empty and fill blood into the ventricles. The AV node detects the atrial depolarization from the SA node and, in turn, relays the depolarization impulse into the ventricles via the bundle of His and Purkinje fibers following a brief conduction delay. The His-Purkinje system begins at the AV node and follows along the membranous interatrial septum toward the tricuspid valve through the AV septum and into the membranous interventricular septum. At about the middle of the interventricular septum, the His-Purkinje system splits into right and left branches, which straddle the summit of the muscular part of the interventricular septum.

Abnormal rhythms generally referred to as arrhythmia can occur in the heart. Cardiac arrhythmias arise when the pattern of the heartbeat is changed by abnormal impulse initiation or conduction in the myocardial tissue. The term tachycardia is used to describe an excessively rapid heartbeat resulting from repetitive stimulation of the heart muscle. Such disturbances often arise from additional conduction pathways that are present within the heart either from a congenital developmental abnormality or an acquired abnormality, which changes the structure of the cardiac tissue, such as a myocardial infarction.

A common arrhythmia is Wolff-Parkinson-White syndrome (W-P-W). The cause of W-P-W is generally believed to be the existence of an anomalous conduction pathway or pathways that connect the atrial muscle tissue directly to the ventricular muscle tissue, thus bypassing the normal His-Purkinje system. These pathways are usually located in the fibrous tissue that connects the atrium and the ventricle.

Atrial arrhythmia may also occur. Three of the most common atrial arrhythmia are ectopic atrial tachycardia, atrial fibrillation, and atrial flutter. Atrial fibrillation can cause significant patient discomfort and even death because of a number of associated problems, including e.g., an irregular heart rate (which causes patient discomfort and anxiety), loss of synchronous atrioventricular contractions (which compromises cardiac hemodynamics, resulting in varying levels of congestive heart failure) and stasis of blood flow (which increases the likelihood of thromboembolism).

In the past, problems associated with arrhythmia have been treated with pharmacological treatment. Such treatment may not be effective in all patients and is frequently plagued with side effects, including, e.g., dizziness, nausea, vision problems, and other difficulties.

Alternatively, such disturbances are treated by identifying the conductive pathways and then severing part of this pathway by destroying these cells, which make up a portion of the pathway. Traditionally, this has been done by either cutting the pathway surgically; freezing the tissue, thus destroying the cellular membranes; or by heating the cells, thus denaturing the cellular proteins. The resulting destruction of the cells eliminates their electrical conductivity, thus destroying, or ablating, a certain portion of the pathway. By eliminating a portion of the pathway, the pathway may no longer maintain the ability to conduct, and the tachycardia ceases.

Catheters are a common medical tool that has been used for many years. They are employed, e.g., for medical procedures to examine, diagnose, and treat while positioned at a specific location within the body that is otherwise inaccessible without more invasive procedures. In such procedures, a catheter is first inserted into a vessel near the surface of the body and the guided to a specific location within the body. For example, a catheter may be used to convey an electrical stimulus to a selected location within the human body or a catheter with sensing electrodes may be used to monitor various forms of electrical activity in the human body.

Catheters have increasingly become a common medical procedure for the treatment of certain types of cardiac arrhythmia. Catheter ablation is based on the idea that by ablation (i.e., destroying) abnormal tissue areas in the heart, its electrical system can be repaired and the heart will return to a normal rhythm. During catheter ablation, the catheter is typically inserted in an artery or vein in the leg, neck, or arm of the patient and then threaded, sometimes with the aid of a guide wire or introducer, through the vessels until a distal tip of the catheter reaches the desired location for the medical procedure in the heart.

Most often, cardiac ablation is used to treat supraventricular tachycardias, or SVTs. Types of SVTs are atrial fibrillation, atrial flutter, AV nodal reentrant tachycardia, AV reentrant tachycardia, and atrial tachycardia. Less frequently, ablation can treat heart rhythm disorders that begin in the heart's lower chambers, known as the ventricles. The most common, ventricular tachycardia may also be the most dangerous type of arrhythmia because it can cause sudden cardiac death. For patients at risk for sudden cardiac death, ablation often is used along with an implantable cardioverter device (ICD). The ablation decreases the frequency of abnormal heart rhythms in the ventricles and therefore reduces the number of ICD shocks a patient may experience. For many types of arrhythmias, catheter ablation is successful in 90-98 percent of cases, thus eliminating the need for open-heart surgeries or long-term drug therapies.

During conventional catheter ablation procedures, an energy source is in contact with cardiac tissue to heat the tissue and create a permanent scar or lesion that is electrically inactive or non-contractile. These lesions are designed to interrupt existing conduction pathways commonly associated with arrhythmias within the heart. The particular area for ablation depends on the type of underlying arrhythmia. One common ablation procedure treats atrioventricular nodal reentrant tachycardia (AVNRT). The use of electrode catheters for ablating specific locations within the heart has also been disclosed in, e.g., U.S. Pat. Nos. 4,641,649, 5,228,442, 5,231,995, 5,263,493, and 5,281,217.

Many variations of ablations procedures are known. For example, ablation of fast or slow AV nodal pathways is disclosed in Singer et al., Catheter Ablation for Arrhythmias, Clinical Manual of Electrophysiology, 421-431 (1993).

Another medical procedure using ablation catheters with sheaths to ablate accessory pathways associated with W-P-W using both a transseptal and retrograde approach is discussed in Saul et al., Catheter Ablation of Accessory Atrioventricular Pathways in Young Patients: Use of long vascular sheaths, the transseptal approach and a retrograde left posterior parallel approach, *Journal of the American College of Cardiology,* 21(3), 571-583 (1993). Additional catheter ablation procedures are disclosed in Swartz, Radiofrequency Endocardial Catheter Ablation of Accessory Atrioventricular Pathway Atrial Insertion Sites, *Circulation,* 87 (2), 487-499 (1993).

Ablation of a specific target requires precise placement of the ablation catheter within the heart. Precise positioning of the ablation catheter is especially difficult due the physiology of the heart, particularly since the heart continues to beat throughout the ablation procedures. Typically, the choice of placement of the catheter is determined by a combination of electrophysiological guidance and fluoroscopy. Fluoroscopy is placement of the catheter in relation to known features of the heart, which are marked by radiopaque diagnostic catheters that are placed in or at known anatomical structures, such as the coronary sinus, high right atrium, and the right ventricle.

Ablation procedures using guiding introducers to direct an ablation catheter to a particular location in the heart for treatment of atrial arrhythmia have been disclosed in, e.g., U.S. Pat. Nos. 5,427,119, 5,497,774, 5,564,440, 5,575,766, 5,628, 316, and 5,640,955. During these procedures, ablation lesions are produced in the heart.

A variety of energy sources can be used to supply the energy necessary to ablate cardiac tissue and create a permanent lesion. Such energy sources include direct current, laser, microwave, and ultrasound. Because of problems associated with the use of DC current, radiofrequency (RF) has become the preferred source of energy for ablation procedures. The use of RF energy for ablation has been disclosed, e.g., in U.S. Pat. Nos. 4,945,912, 5,242,441, 5,246,438, 5,281,213, 5,281, 218, and 5,293,868. The use of RF energy with an ablation catheter contained within a transseptal sheath for the treatment of W-P-W in the left atrium is disclosed in Swartz et al., Radiofrequency Endocardial Catheter Ablation of Accessory Atrioventricular Pathway Atrial Insertion Sites, *Circulation,* 87: 487-499 (1993). See also Tracey, Radio Frequency Catheter Ablation of Ectopic Atrial Tachycardia Using Paced Activation Sequence Mapping, *J. Am. Coll. Cardiol.* 21: 910-917 (1993).

Conventional ablation procedures use a single electrode secured to the tip of an ablation catheter. It has become increasingly more common to use multiple electrodes affixed to the catheter body. Such ablation catheters often contain a distal tip electrode and a plurality of ring electrodes as disclosed in, e.g., U.S. Pat. Nos. 4,892,102, 5,228,442, 5,327, 905, 5,354,297, 5,487,385, and 5,582,609.

During conventional ablation procedures, the ablating energy is delivered directly to the cardiac tissue by an electrode on the catheter placed against the surface of the tissue to raise the temperature of the tissue to be ablated. The increase in tissue temperature also results in a rise in the temperature of blood surrounding the electrode. This rise in temperature often results in the formation of coagulum on the electrode, which in turn reduces the efficiency of the ablation electrode. Thus, to achieve efficient and effective ablation, coagulation of blood should be avoided. This coagulation problem can be especially significant when linear ablation lesions or tracks are produced because such linear ablation procedures take more time than ablation at only a single location.

The formation of linear lesions within a heart via conventional ablation tip electrode requires use of procedures such as e.g., a "drag burn." A "linear lesion" means an elongate, continuous lesion, which may be straight or curved, that blocks electrical conduction. During a "drag burn" procedure, while energy is supplied to the electrode, the electrode is drawn across the tissue to be ablated, producing a line of ablation. Alternatively, a series of points of ablation are formed in a line created by moving the tip electrode incremental distances across the cardiac tissue. The effectiveness of these procedures depends on a number of variables such as e.g., (i) the position and contact pressure of the tip electrode of the ablation catheter against the cardiac tissue, (ii) the time that the tip electrode of the ablation catheter is placed against the tissue, (iii) the amount of coagulum formed as a result of heat generated during the ablation procedure, and (iv) other variables associated with a beating heart, especially an erratically beating heart. An uninterrupted track of cardiac tissue needs to be ablated as unablated tissue or incompletely ablated tissue may remain electrically active, thereby permitting the continuation of stray circuits that cause arrhythmia.

More efficient ablation can be achieved if a linear lesion of cardiac tissue is formed during a single ablation procedure. The production of linear lesions in the heart by use of an ablation catheter is disclosed in, e.g., U.S. Pat. Nos. 5,487, 385, 5,582,609, and 5,676,662. A specific series of linear lesions formed in the atria for the treatment of atrial arrhythmia are disclosed in U.S. Pat. No. 5,575,766.

Physical contact of the cardiac tissue with an electrode of the ablation catheter is typically used to perform these procedures on electrically inactive or non-contractile tissue. Conventional tip electrodes with adjacent ring electrodes cannot perform this type of procedure, however, due to the high amount of energy necessary to ablate sufficient tissue to produce a complete linear lesion. In addition, conventional ring electrode ablation may leave holes or gaps in a lesion, which can provide a doorway for the creation of unwanted circuits.

U.S. Pat. No. 5,334,193 discloses an ablation catheter for use in the heart that contains a pair of intertwined helical electrodes. The helically wound electrode is affixed to the surface of the catheter body over a distance of about eight centimeters from the distal tip of the catheter body. Other helical electrodes are disclosed in WO 95/10319 as well as U.S. Pat. Nos. 4,161,952, 4,776,334, 4,860,769, 4,934,049, 5,047,026, and 5,542,928.

As discussed a variety of energy such as radiofrequency (RF), microwave, ultrasound, and laser energy have been used for ablation. With RF energy, a catheter with a conductive inner core and a metallic tip are placed in contact with the myocardium and a circuit is completed with a patch placed on the patient's body behind the heart. The catheter is coupled to a RF generator such that application of electrical energy creates localized heating in the tissue adjacent to the distal (emitting) electrode. The peak tissue temperatures during catheter delivered application of RF energy to the myocardium occur close to the endocardial surface, such that the lesion size produced is limited by the thermodynamics of radiant heat spread from the tip. The amount of heating which occurs is dependent on the area of contact between the electrode, and the tissue and the impedance between the electrode and the tissue. The higher the impedance, the lower the amount of energy transferred into the tissue.

During RF catheter ablation, local temperature elevation can result in coagulum formation on the ablation electrode, resulting in impedance rise. As the impedance increases, more energy is passed through the portion of the tip without coagulation, creating even higher local temperatures and further increasing coagulum formation and the impedance. Finally, enough blood coagulates onto the tip that no energy passes into the tissue. The catheter must now be removed from the vascular system, the tip area cleaned and the catheter repositioned within the heart at the desired location. Not only can this process be time consuming, but also it may be difficult to return to the previous location because of the reduced electrical activity in the regions, which have previously been ablated. A recent study has also demonstrated the formation of a so-called soft thrombus during experimental ablations (Demonlin et al., *Pacing Clin. Electrophysiol.* 25(8): 1219-1222 (2002)). The formation of the so-called soft thrombus results from heat induced protein denaturation and aggregation and occurs independent of heparin concentration in serum.

To prevent the occurrence of, e.g., soft thrombus, blood coagulation, and steam pop during ablation, the catheter may be cooled by passing a fluid through the catheter during ablation. Saline irrigation is an effective way to cool the ablation electrode and keep efficient flow around the electrode to prevent blood coagulation. Furthermore, the surface cooling that results from the saline irrigation reduces heating at the point of highest current density where excessive temperatures would normally produce charring, crater formation and impedance rises (Thomas et al., *Europace* 6: 330-335 (2004)). Open irrigated ablation catheters are currently the most common irrigated catheters in the electrophysiology field. Examples of these devices include Thermocool® by Biosense Webster and CoolPath® by Irvine Biomedical.

In order to effectively cool the electrode at any possible catheter electrode orientation, it is important to maintain a saline flow rate of, for example, 20-30 ml/minute. The high saline volume can result in a deterioration of the patient's condition. In part, this occurs due to hemodilution affecting the volume, placing additional stresses on the heart/circulatory system. This can lead to edema and swelling. Thus, there is a need for a method of cooling the electrode during ablation without using an excess of saline in irrigation.

BRIEF SUMMARY OF THE INVENTION

It is desirable to be able to provide an improved ablation catheter for reciprocating irrigation flow.

In a first embodiment of the invention, the irrigated ablation catheter comprises an electrode having an inner cavity and one or more passages from the inner cavity to an outer surface of the electrode; an elongate body having a distal end, a proximal end, and a lumen; and an alternating element inside the lumen to maintain a reciprocating flow of blood into and out of the inner cavity of the electrode.

The alternating element inside the first embodiment of the invention may be a slideable plunger actuated at the proximal end of the body, a slideable piston actuated hydraulically at the proximal end of the body, an inflatable balloon actuated hydraulically at the proximal end of the body, or a solenoid and a spring.

A second embodiment of the invention is a method of cooling an ablation electrode using reciprocating flow comprising an intake step of admitting blood into an inner cavity of the electrode and an exhaust step expelling the blood from the inner cavity of the electrode, wherein the volumes of flow into and out of the inner cavity of the electrode are equal in the intake and exhaust steps, respectively.

In the second embodiment of the invention, the flow rate into and out of the inner cavity of the electrode is in the range of about 0.25 cc to 1.0 cc in the intake or exhaust steps.

In the second embodiment of the invention, a cycle consists of an intake step followed by an exhaust step, and the frequency of the steps is in the range of about 30 to 120 cycles per minute.

In the second embodiment of the invention, anticoagulant drugs may be administered to the inner cavity of the electrode.

A third embodiment of the invention is a catheter system to perform ablation on cardiac tissue, comprising: an open irrigated ablation catheter having a body, an electrode coupled to a distal end of the body, a reciprocating member inside the body, and one or more passages disposed distal to the reciprocating member for fluid flow into and out of the body; and a fluid pump providing reciprocating flow to move the reciprocating member inside the body of the catheter toward and away from the one or more passages.

A fourth embodiment of the invention is an ablation catheter comprising: an elongate body having a distal end, a proximal end, and a lumen; an electrode connected to the distal end of the elongate body to form an interior space of the catheter; and a reciprocating member disposed in the interior space of the catheter; wherein one or more passages of the catheter are disposed distal to the reciprocating member for reciprocating fluid flow into and out of a distal region of the interior space of the catheter in response to movement of the reciprocating member in the interior space of the catheter.

In the fourth embodiment of the invention, the reciprocating member may comprise a mechanically driven slidable plunger, a hydraulically driven slidable piston, an inflatable balloon, or an electrically driven slidable piston. The fourth embodiment of the invention may further comprise means for driving the reciprocating member to move in the interior space of the catheter. In a variation of the fourth embodiment, the electrode includes the one or more passages. In another variation of the fourth embodiment, the reciprocating member includes a portion that forms a tight fit in the interior space of the catheter to prevent fluid flow between the distal region of the interior space and a proximal region of the interior space of the catheter. The portion of the reciprocating member may also comprise a bushing. The portion of the reciprocating member may also comprise a slidable tight-fit surface in sliding contact with an inner surface of the catheter.

The foregoing and other aspects, features, details, utilities, and advantages of the present invention will be apparent from

DETAILED DESCRIPTION OF THE INVENTION

Figure 1A:
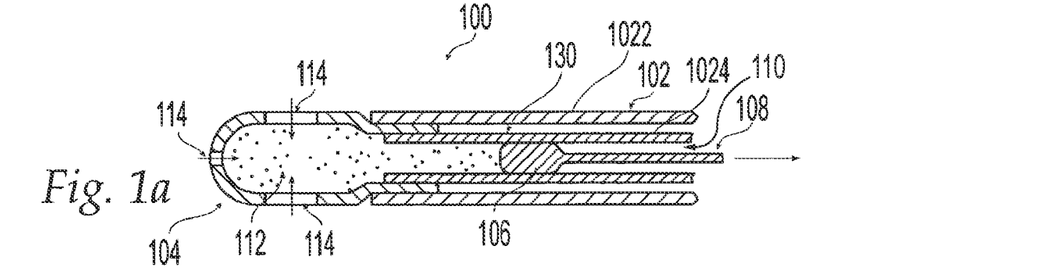
FIG. 1(a) is a cross-sectional view of the electrode and the distal end of the body of an irrigated ablation catheter in which a plunger is used to admit blood into an inner cavity of the electrode.
Figure 1B:
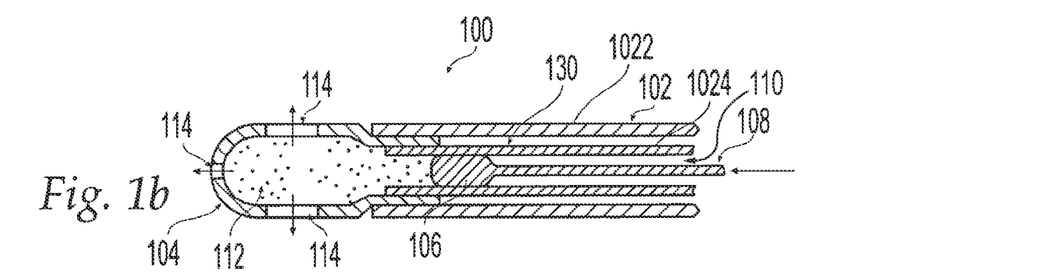
FIG. 1(b) is the cross-sectional view of FIG. 1(a) in which the plunger is used to expel blood from the inner cavity of the electrode.

An embodiment of the invention uses a plunger to cause reciprocating flow of blood into and out of a catheter electrode. Referring to FIGS. 1(a) and 1(b), side elevational views of catheter 100 are shown having a catheter body 102, an electrode 104, a plunger 106, and a plunger shaft 108. Catheter body 102 may be of varying lengths, the length being determined by the application for the catheter 100. Catheter body 102 is preferably made of a flexible durable material suitable for use within the human body, such as nonconductive polymers. Exemplary polymers used for the production of the catheter body include those well-known in the art such as polyolefins, nylons, polytetrafluoroethylene, polyvinylidene fluoride, and fluorinated ethylene-propylene polymers. As appropriate, a braiding is embedded. Catheter body 102 includes outer wall 1022 or 2020, inner wall 1024 or 2024, a large central lumen 110 and an optional annular region 130. Although shown with a double walled body, the body may be single-walled.

The diameter of the catheter is within ranges well-known in the industry. Preferably, the diameter of the catheter body 102 is within the range of about 2 to 14 French (1 French equals ⅓ of a millimeter).

The electrode conductor or conductors, which pass from the proximal end of the catheter through lumen 110 or annular region 130, exit the catheter through an exit port or ports in the surface of catheter body 102, preferably within about 1 to about 5 cm from the distal end of the catheter. Alternatively, the electrode conductor or conductors may be embedded within the inner or outer wall of catheter body 102. The electrode 104 may be a single electrode or a plurality of ring electrodes surrounding the exterior surface of catheter body 102. The electrode 104 has an inner cavity 112 and through holes 114 from the inner cavity to the exterior of the electrode 104.

The purpose of through holes 114 is to allow blood to flow into and out of the inner cavity 112 of the electrode 104 and a portion of the central lumen 110 of the catheter body 102. The blood flow cools the electrode 104 to minimize thrombus.

Plunger shaft 108 may be constructed of any thin stiff corrosion resistant material such as stainless steel and drives a reciprocating motion of plunger 106. The reciprocating motion of plunger shaft 108 may be driven by any means well known in the art. Plunger 106 is preferably fabricated from any elastomer suitable for use in a catheter, although the material(s) of construction is not limited to elastomers. The outer diameter of plunger 106 is closely matched with the inner diameter of catheter body 102 to allow a tight fit, minimizing leakage around plunger 106. FIG. 1(a) shows outflow of blood (designated by arrows pointing into the inner cavity 112 of electrode 104) from the inner cavity 112 of the electrode 104 and a portion of the central lumen 110 of the catheter body 102 as a result of the plunger 106 being driven in the direction of the electrode 104. FIG. 1(b) shows inflow of blood (designated by arrows pointing out of the inner cavity 112 of electrode 104) to the inner cavity 112 of the electrode 104 and a portion of the central lumen 110 of the catheter body 102 as a result of the plunger 106 being driven in the direction away from the electrode 104.

Figure 2A:
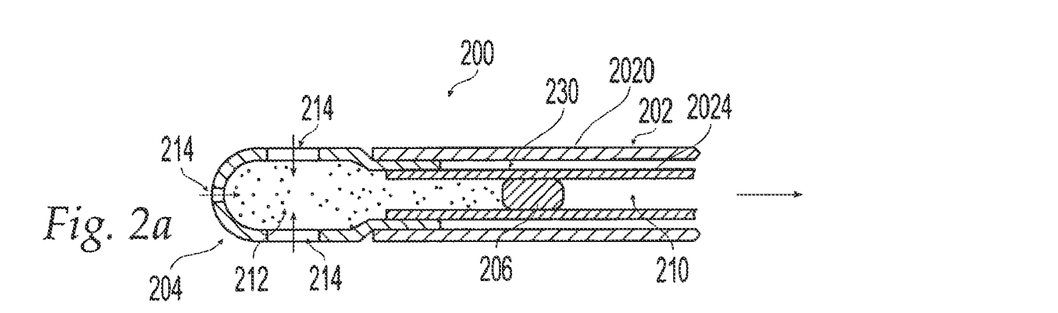
FIG. 2(a) is a cross-sectional view of the electrode and the distal end of the body of an irrigated ablation catheter in which a piston is used to admit blood into an inner cavity of the electrode.
Figure 2B:
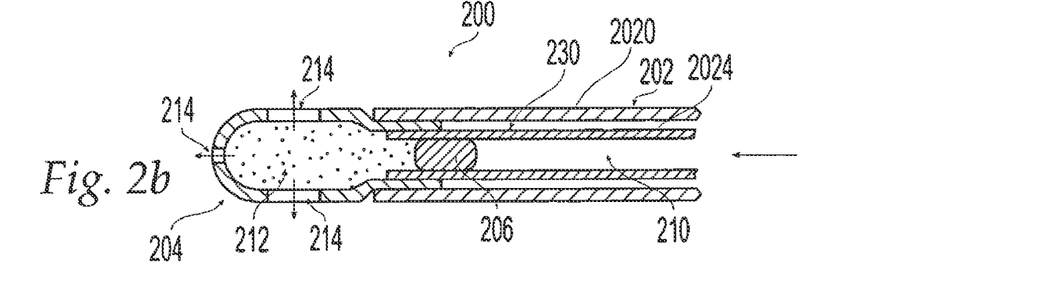
FIG. 2(b) is the cross-sectional view of FIG. 2(a) in which the piston is used to expel blood from the inner cavity of the electrode.

A variation of the embodiment of the invention described above uses a piston to cause reciprocating flow of blood into and out of a catheter electrode. Referring to FIGS. 2(a) and 2(b), side elevational views of catheter 200 are shown having a catheter body 202, an electrode 204, and a piston 206. Catheter body 202 may be of varying lengths, the length being determined by the application for the catheter 200. Catheter body 202 is preferably made of a flexible durable material, including thermoplastics such as nylon, in which a braiding is embedded. Catheter body 202 includes a large central lumen 210. The electrode 204 may be a single electrode or a plurality of ring electrodes surrounding the exterior surface of catheter body 202. The electrode 204 has an inner cavity 212 and through holes 214 from the inner cavity to the exterior of the electrode 204.

The purpose of through holes 214 is to allow blood to flow into and out of the inner cavity 212 of the electrode 204 and a portion of the central lumen 210 of the catheter body 202. The blood flow cools the electrode 204 to minimize thrombus.

The reciprocating motion of piston 206 is driven by a hydraulic fluid such as saline or any other hemo-compatible on the side of piston 206 opposite electrode 204. The hydraulic fluid which alternates between high and low pressure by any means well known in the art to drive piston 206 toward electrode 204 and allow the blood pressure to drive piston 206 away from the electrode. The outer diameter of plunger 206 is closely matched with the inner diameter of catheter body 202 to allow a tight fit, minimizing leakage of hydraulic fluid around plunger 206. FIG. 2(a) shows outflow of blood (designated by arrows pointing into the inner cavity 212 of electrode 204) from the inner cavity 212 of the electrode 204 and a portion of the central lumen 210 of the catheter body 202 as a result of the piston 206 being driven in the direction of the electrode 204. FIG. 2(*b*) shows inflow of blood (designated by arrows pointing out of the inner cavity 112 of electrode 104) to the inner cavity 212 of the electrode 204 and a portion of the central lumen 210 of the catheter body 202 as a result of the piston 206 being driven in the direction away from the electrode 204.

Figure 3A:
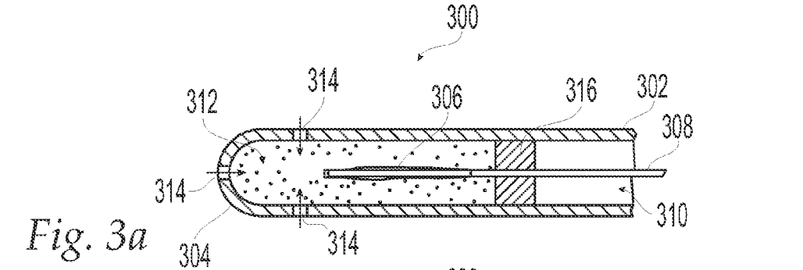
FIG. 3(a) is a cross-sectional view of the electrode and the distal end of the body of an irrigated ablation catheter in which a balloon is used to admit blood into an inner cavity of the electrode.
Figure 3B:
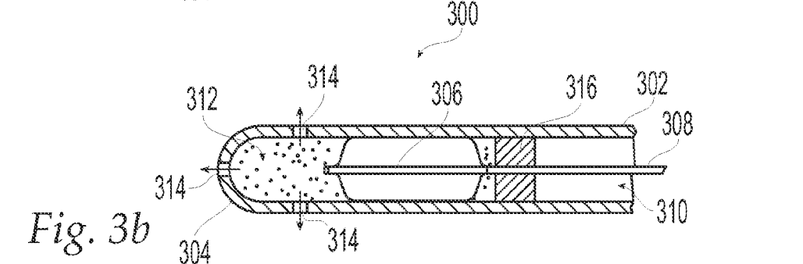
FIG. 3(b) is the cross-sectional view of FIG. 3(a) in which the balloon is used to expel blood from the inner cavity of the electrode.

Another variation of the embodiment of the invention described above uses a balloon to cause reciprocating flow of blood into and out of a catheter electrode. Referring to FIGS. 3(*a*) and 3(*b*), side elevational views of catheter 300 are shown having a catheter body 302, an electrode 304, a balloon 306, a tube 308, and a bushing 316. Catheter body 302 may be of varying lengths, the length being determined by the application for the catheter 300. Catheter body 302 is preferably made of a flexible durable material, including thermoplastics such as nylon, in which a braiding is embedded. Catheter body 302 includes a large central lumen 310. The electrode 304 may be a single electrode or a plurality of ring electrodes surrounding the exterior surface of catheter body 302. The electrode 304 has an inner cavity 312 and through holes 314 from the inner cavity to the exterior of the electrode 304.

The purpose of through holes 314 is to allow blood to flow into and out of the inner cavity 312 of the electrode 304 and a portion of the central lumen 310 of the catheter body 302. The blood flow cools the electrode 304 to minimize thrombus.

Tube 308 may be constructed of any flexible material suitable for forming tubing such as polymers and rubber. Bushing 316 may be made of any material suitable for forming a seal in the concentric area between the inner diameter of catheter body 302 and the outer diameter of tube 308. Bushing 316 divides the portion of the lumen 312 that is exposed to blood flow from the portion of the lumen 312 that is not exposed to blood flow.

Balloon 306 is alternately inflated and deflated to propel blood flow into and out of the inner cavity 312 of the electrode 304 and a portion of the central lumen 310 of the catheter body 302. Inflation of balloon 306 is accomplished by pumping a fluid into balloon 306. Releasing pressure of the fluid inside balloon 306 allows blood pressure to deflate balloon 306. Pressurization of the fluid within balloon 306 may be accomplished by compressors, pumps, or any other means well known in the art. The fluid used to inflate the balloon is preferentially saline, but may be air, another gas, water, or any other fluid known to be safe in the application.

FIG. 3(*a*) shows inflow of blood into the inner cavity 312 of the electrode 304 and a portion of the central lumen 310 of the catheter body 302 as a result of balloon 306 being deflated. FIG. 3(*b*) shows outflow of blood from the inner cavity 312 of the electrode 304 and a portion of the central lumen 310 of the catheter body 302 as a result of balloon 306 being inflated.

Figure 4:
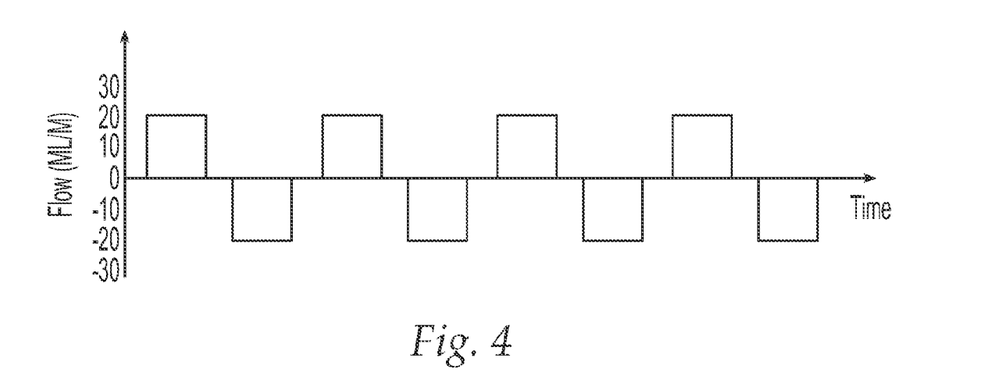
FIG. 4 is an illustration of reciprocating flow in the catheters of FIGS. 1-3 in which the sum of inflow and outflow is zero.

FIG. 4 is a diagram showing blood flow into and out of an electrode tip over time. As shown, flow into and out of the electrode is approximately constant in opposite directions with inflow and outflow strokes, with pauses between strokes. The sum of the inflows and outflows is zero.

Figures 5, 6:
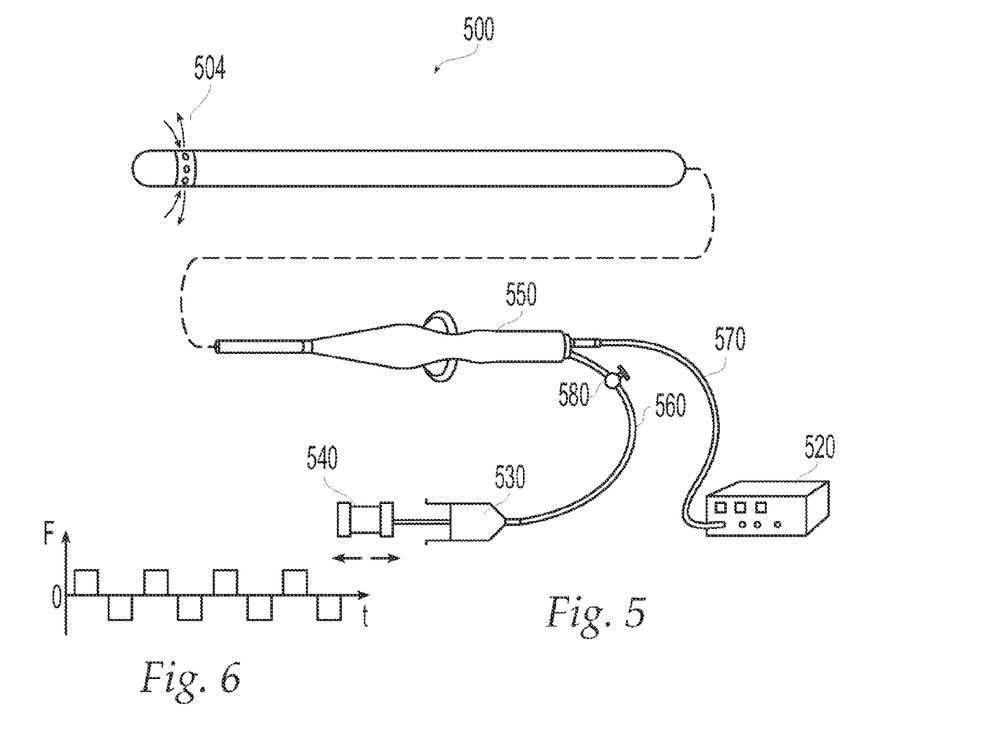
FIG. 5 is a depiction of an RF ablation system using reciprocating flow using a conventional irrigated ablation catheter.
FIG. 6 is a chart depicting flow rate over time through a syringe pump of FIG. 5.

FIG. 5 shows a complete catheter set-up using one of the three embodiments. The set-up comprises catheter 500 with electrode 504, RF generator 520, syringe pump 530, reciprocating stepper motor 540, proximal end control handle 550, tubing 560, RF generator leads 570, and valve 580.

A user maneuvers the distal end (end with electrode 504) by manipulating proximal end control handle 550 by any means well-known in the art including, but not limited to, pull wires When electrode 504 is in the proper location, the user activates RF generator 520 and reciprocating stepper motor 540. With the second and third embodiments described above, the reciprocating stepper motor 540 moves a plunger in syringe pump 530 back and forth to pump and withdraw a hydraulic fluid through tube 560 to cause a piston to reciprocate or a balloon to inflate and deflate within a lumen of the catheter 500. The first embodiment would dispense with the syringe pump 530 and the reciprocating stepper motor 540 would drive a plunger shaft directly. The RF generator provides a signal through RF generator leads to electrode 504 to allow electrode 504 to perform ablation. Valve 580 may be used to stop fluid flow to the catheter. Anticoagulant drugs may also be administered by a separate pump and tube leading to the region of the lumen of catheter 500 adjacent to electrode 504 (i.e., on the electrode side of the piston, pump, or bushing).

FIG. 6 is a diagram depicting the signal to a reciprocating stepping motor. "F" on the vertical axis represents fluid flow rate through the syringe pump and "t" on the horizontal axis represents time.

Figure 7A:
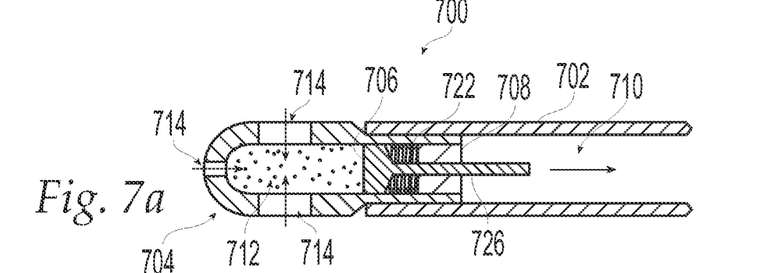
FIG. 7(a) is a cross-sectional view of the electrode and the distal end of the body of an irrigated ablation catheter in which a solenoid is used to drive a plunger to admit blood into the inner cavity of the electrode.
Figure 7B:
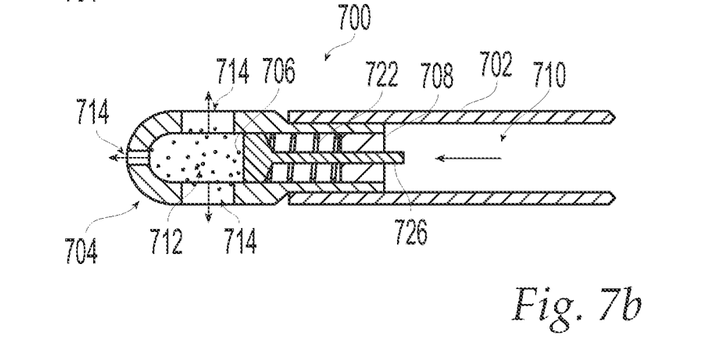
FIG. 7(b) is the cross-sectional view of FIG. 7(a) in which a spring is used to drive the plunger to expel blood from the inner cavity of the electrode.

Another variation of the embodiment of the invention described above uses a balloon to cause reciprocating flow of blood into and out of a catheter electrode. Referring to FIGS. 7(*a*) and 7(*b*), side elevational views of catheter 700 are shown having a catheter body 702, an electrode 704, a plunger 706, a solenoid 708, and a spring 722. Catheter body 702 may be of varying lengths, the length being determined by the application for the catheter 700. Catheter body 702 is preferably made of a flexible durable material, including thermoplastics such as nylon, in which a braiding is embedded. Catheter body 702 includes a large central lumen 710. The electrode 704 may be a single electrode or a plurality of ring electrodes surrounding the exterior surface of catheter body 702. The electrode 704 has an inner cavity 712 and through holes 714 from the inner cavity to the exterior of the electrode 704.

The purpose of through holes 714 is to allow blood to flow into and out of the inner cavity 712 of the electrode 704 and a portion of the central lumen 710 of the catheter body 702. The blood flow cools the electrode 704 to minimize thrombus.

Electrical current is provided to solenoid 708 through leads (not shown) running the length catheter body 702 either within central lumen 710 or embedded in catheter body 710. Activation of solenoid 708 pulls stem 726 of plunger 706 in the proximal direction of catheter body against the biasing force of spring 722. Spring 722 is located surrounding stem 726 on the distal side of solenoid 708. The movement of plunger 706 in the proximal direction draws blood into inner cavity 712 of electrode 704 as shown in FIG. 7(*a*).

Stopping electrical current flow to solenoid 708 results in spring 722 pushing plunger 706 in the distal direction to push blood out of inner cavity 712 of electrode 704 as shown in FIG. 7(*b*). A periodically interrupted flow of current to solenoid 708 alternately draws in and expels blood from inner cavity 712 of electrode 704 to provide cooling flow.

Although the embodiments of this invention have been described above with a certain degree of particularity, those skilled in the art could make numerous alterations to the disclosed embodiments without departing from the spirit or scope of this invention. For example, any means of causing a reciprocating flow could be used. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting.

Changes in detail or structure may be made without departing from the spirit of the invention as defined in the appended claims.

What is claimed is:

1. An irrigated ablation catheter comprising:
   a handle;
   an electrode having an inner cavity and one or more passages from the inner cavity to an outer surface of the electrode;
   an elongate body defining a longitudinal axis and having a distal end, a proximal end coupled to the handle, and a lumen; and
   a longitudinally-alternating element disposed inside the lumen at the distal end of the elongate body and configured to maintain a reciprocating flow of fluid into and out of the inner cavity of the electrode.

2. The irrigated ablation catheter of claim 1, wherein the alternating element is a slideable plunger actuated at the proximal end of the elongate body.

3. The irrigated ablation catheter of claim 1, wherein the alternating element is a slideable piston actuated hydraulically at the proximal end of the elongate body.

4. The irrigated ablation catheter of claim 1, wherein the alternating element is a plunger driven in one direction by a solenoid and in an opposite direction by a spring.

5. A catheter, comprising:
   a handle;
   an elongate body coupled to the handle and defining a longitudinal axis;
   an electrode coupled to a distal portion of the elongate body; and
   a reciprocating member disposed inside the distal portion of the elongate body and configured to move longitudinally with respect to the elongate body.

6. The catheter of claim 5, further comprising one or more passages disposed distal to the reciprocating member for fluid flow into and out of the elongate body, wherein the reciprocating member is configured to move with respect to the one or more passages.

7. The catheter of claim 6, further comprising a fluid pump providing reciprocating flow to move the reciprocating member inside the elongate body toward and away from the one or more passages.

8. The catheter of claim 5, wherein the reciprocating member is positioned proximate the distal portion of the elongate body.

9. An ablation catheter comprising:
   a handle;
   an elongate body defining a longitudinal axis and having a distal end, a proximal end coupled to the handle, and a lumen;
   an electrode connected to the distal end of the elongate body to form an interior space of the catheter;
   a longitudinally-reciprocating member disposed in the interior space of the catheter; and
   one or more passages disposed distal to the reciprocating member for reciprocating fluid flow into and out of a distal region of the interior space of the catheter in response to movement of the reciprocating member in the interior space of the catheter.

10. The ablation catheter of claim 9, wherein the reciprocating member comprises a mechanically driven slidable plunger.

11. The ablation catheter of claim 9, wherein the reciprocating member comprises a hydraulically driven slidable piston.

12. The ablation catheter of claim 9, wherein the reciprocating member comprises an electrically driven slidable piston.

13. The ablation catheter of claim 9, further comprising means for driving the reciprocating member to move in the interior space of the catheter.

14. The ablation catheter of claim 9, wherein the electrode includes the one or more passages.

15. The ablation catheter of claim 9, wherein the reciprocating member includes a portion that forms a tight fit in the interior space of the catheter to prevent fluid flow between the distal region of the interior space and a proximal region of the interior space of the catheter.

16. The ablation catheter of claim 15, wherein the portion of the reciprocating member comprises a slidable tight-fit surface in sliding contact with an inner surface of the catheter.

17. The ablation catheter of claim 9, wherein the reciprocating member is positioned proximate the distal end of the elongate body.

* * * * *